United States Patent
Tabata et al.

(10) Patent No.: US 7,476,648 B1
(45) Date of Patent: Jan. 13, 2009

(54) VESSEL EMBOLIC MATERIAL COMPRISING HYDROGEL AND THERAPY WITH THE USE THEREOF

(75) Inventors: Yasuhiko Tabata, 8-16, Biwadai 3-chome, Uji-shi, Kyoto (JP) 611-0024; Susumu Miyamoto, 23-3, Matsugasaki naka-machi, Sakyo-ku, Kyoto-shi, Kyoto (JP) 606-0926

(73) Assignees: Kaken Pharmaceutical Company, Ltd. (JP); Susumu Miyamoto (JP); Yasuhiko Tabata (JP)

( * ) Notice: Subject to any disclaimer, the term of this patent is extended or adjusted under 35 U.S.C. 154(b) by 274 days.

(21) Appl. No.: 10/111,483

(22) PCT Filed: Oct. 26, 2000

(86) PCT No.: PCT/JP00/07478

§ 371 (c)(1),
(2), (4) Date: Aug. 14, 2002

(87) PCT Pub. No.: WO01/30411

PCT Pub. Date: May 3, 2001

(30) Foreign Application Priority Data

Oct. 26, 1999 (JP) .................................. 11-303609

(51) Int. Cl.
*A61K 38/00* (2006.01)
*A61K 38/18* (2006.01)
(52) U.S. Cl. ............................................ 514/2; 514/12
(58) Field of Classification Search ...................... 514/2; 530/350
See application file for complete search history.

(56) References Cited

U.S. PATENT DOCUMENTS 6,831,058 B1 * 12/2004 Ikada et al. ..................... 514/2

FOREIGN PATENT DOCUMENTS

| EP | 0 132 983 | 2/1985 |
| EP | 0 702 959 | 3/1996 |
| JP | 60-222045 | 11/1985 |
| JP | 11-076249 | 3/1999 |
| JP | 11-169703 | 6/1999 |
| WO | WO 95/09659 | 4/1995 |
| WO | WO 99/47047 | * 9/1999 |

OTHER PUBLICATIONS

Cai et al. Biomaterials 2005; 26: 6054-5057.*
Fujita et al. Journal of Surgical Research; 126: 27-33.*
Hosaka et al. Molecular Cardiology. 2004; 110: 3322-3328.*
Ikeda et al. No Shinkei Geka. 1984; 12: 1151-8—abstract only; original article in Japanese.*
Yasuhara et al. J Neurosurg. 2002; 97: 697-700.*
Jang et al. J Korean Neurosur Soc. 2006; 40: 293-295.*
Kallmes et al., *Radiology*, 207(2):519-523 (1998).
Futami, et al., *Stroke*, 26(9):1649-1654 (1995).

* cited by examiner

*Primary Examiner*—Elizabeth C. Kemmerer
*Assistant Examiner*—Christina Borgeest
(74) *Attorney, Agent, or Firm*—Nixon Peabody LLP

(57) ABSTRACT

According to the present invention, a vessel embolic material comprising a hydrogel containing a cell growth factor, which is applicable to embolic operations for various vascular disorders, excellent in high adaptability to a living body, can be easily handled, ensures the occlusion of the affected part and can maintain the occlusion for a long time, and a method of treatment using the same can be provided.

7 Claims, 5 Drawing Sheets

VESSEL EMBOLIC MATERIAL COMPRISING HYDROGEL AND THERAPY WITH THE USE THEREOF

TECHNICAL FIELD

The present invention comprises a hydrogel containing a cell growth factor, and relates to a vessel embolic material treating the blood vessel disorders such as aneurysm, arteriovenous malformation, spinal arteriovenous malformation, meningeal arteriovenous fistula, and the like by proliferating self organism tissue by sustained release thereof, and a method of treatment using the same.

BACKGROUND ART

Cerebral aneurysm is knob, which one per 100 of adults has in artery, has a diameter of about 1 mm to about 20 mm, and genesis site ranges various cerebral arteries. Among these, about 30% elapses without rupture, about 70% is ruptured to cause subarachnoid hemorrhage and intracerebral hemorrhage. Further, the arteriovenous malformation is most frequently observed among cerebral vessel malformation and is most widely known. It comprises the integration of blood vessels having arteriovenous anactomasis of a woven and dilated inflow blood vessel and an effluent blood vessel and their intervals, and causes intracerebral hemorrhage, subarachnoid hemorrhage, epilepsy, and progressive neural functional dropout which are attacked in younger generation.

In the treatment of these cerebral vessel disorders, the rupture of aneurysm is prevented by clipping cerebral aneurysm from outside with an operation, and intravascular surgical treatment applying a vessel catheter is carried out without operational invasion. The treatment applying vessel catheter is called as embolic operation, a minute catheter is selectively put in the affected part of cerebral artery, the affected part is occluded by an embolic substance which is introduced from said catheter, the abnormal bloodstream of lesion part is intercepted to solidify the affected part, and the restoration of blood vessel is carried out. It is carried out for the treatment of cerebral aneurysm, arteriovenous malformation and the like.

A coil made of platinum and a cyanoacrylate-based adhesive material and the like have been conventionally used as the embolic material for vessel embolic.

However, there are cases in which the conventional treatment of clipping cerebral aneurysm from outside cannot adequately occlude depending on the genesis site and form of aneurysm. On the other hand, the embolic operation of inserting a coil in aneurysm using a vessel catheter has a problem that the coil is compressed in the lapse of time, a gap is generated in the aneurysm, and it is easily fractured again. Further, since an adhesive agent is abruptly solidified in case of the cyanoacrylate-based adhesive embolic material, it is difficult to successfully replenish the embolic material in knob. Further, there is a possibility that the edge of a catheter is adhered on the inner wall of blood vessel, and skill is required for the treatment. Further, there is a problem that formalin which is the decomposition product of a material itself stimulates greatly organism.

In order to solve these problems, it is the object of the present invention to provide a vessel embolic material which can be adopted to the embolic operation of vessel disorders having various sites and forms, is excellent in adaptability to a living body and easily treated, can surely occlude the affected part, and can keep occlusion condition for a long time; and a treatment using thereof.

Under these circumstances, the present inventors considered that cell growth factor is gradually released from an biological absorbent hydrogel and the lumen of blood vessel is filled up with self-organism tissue thereby in order to solve the above-mentioned problems. The present inventors have extensively studied in order to realize this, and as a result, have found out that the biological absorbent hydrogel containing a cell growth factor is useful as a vessel embolic material to completed the present invention.

DISCLOSURE OF THE INVENTION

Namely, the present invention relates to a vessel embolic material comprising a hydrogel which contains a cell growth factor for sustained release thereof.

Further, the present invention relates to a method of treatment of vessel disorders comprising adopting a hydrogel containing the above-mentioned cell growth factor to the affected site.

BEST MODE FOR CARRYING OUT THE INVENTION

Figure 1:
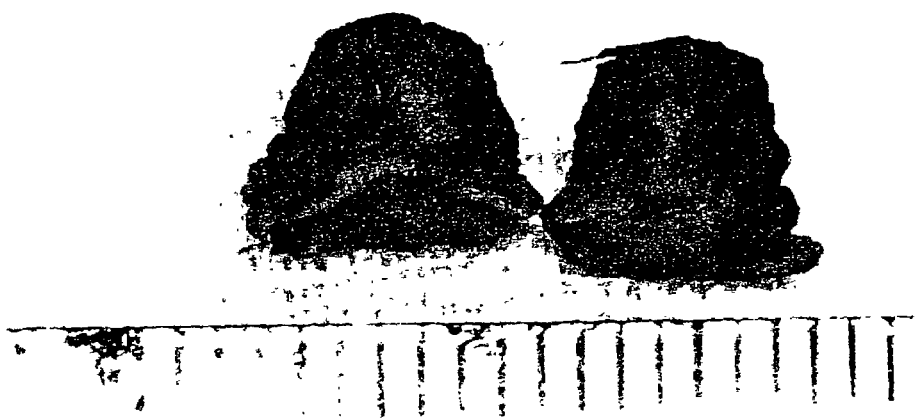
FIG. 1 is a photograph showing the inside of the experimental aneurysm treated with a gelatin hydrogel (water content: 98%) containing bFGF.

The present invention will be illustrated in detail below.

The vessel embolic material of the present invention is a material in which a cell growth factor is contained in a hydrogel. The cell growth factor adopted in the present invention includes those generally called as the proliferating (growth) factor of cell such as bFGF (a basic fibroblast growth factor), aFGF (an acidic fibroblast growth factor), PDGF (a platelet-derived growth factor), TGF-β1 (a transforming growth factor β1), VEGF (a vascular endotheliocyte growth factor) and the like, or cells constituting blood vessels such as vascular endotheliocyte, smooth muscle cell and the like, or substances having activity to grow their peripheral cells such as, for example, interleukin, cytokine, physiologically active peptides, and the like. It is most preferable to use bFGF among these in the present invention.

The hydrogel in which the cell growth factor is to be contained is not specifically limited so long as it is a hydrogel having a property to be absorbed by a living body, and there may be mentioned, for example, gelatin, collagen, starch, pectin, hyaluronic acid, chitin, chitosan or alginic acid and the derivative of these materials, and preferably a hydrogel from gelatin and the like. The hydrogel may be obtained by chemically crosslinking the above-mentioned various hydrogel materials, or may be obtained by treating it with a gelation agent such as a metal salt, an inorganic salt or the like.

The gelatin to be used in the present invention is not specifically limited, and may be one usually available. There may be mentioned, for example, a gelatin with an isoelectric point of 4.9 which was treated with an alkali, and a gelatin with an isoelectric point of 9.0 which was treated with an acid.

The hydrogel of the present invention is particularly preferably a crosslinked gelatin hydrogel which is obtained by chemically treating gelatin. As the method of chemically crosslinking a gelatin, conventionally known methods can be used. For example, as a crosslinking agent of gelatin, those being not toxic to organism may be used, and include glutaraldehyde, 1-ethyl-3-(3-diemthylaminopropyl) carbodiimide hydrochloride, and the like. Further, the hydrogel may be obtained by crosslinking gelatin by heat treatment or ultraviolet irradiation.

A form of the hydrogel to be used in the present invention is not specifically limited so long as it is introduced in the restoration part of the affected blood vessel or around thereof, and, for example, is a rectangular shape, a cylindrical shape, a sheet shape, a disc shape, a spherical shape, a granular shape and a paste shape.

A water content of the hydrogel in the present invention is about 50 to 99 W/W %, preferably 90 to 99 W/W %, and particularly preferably 95 to 98 W/W %.

In order to let the above-mentioned hydrogel contain the cell growth factor such as bFGF or the like, for example, a bFGF aqueous solution is impregnated in a dried hydrogel by dropwise addition, or the dried hydrogel is suspended in the bFGF aqueous solution to be swollen again.

The bFGF which can be used in the present invention includes those extracted from organs such as hypophysis cerebri, brain, retina, lutein, adrenal and the like, those produced by a genetic engineering procedure such as recombinant DNA technology or the like, further, those which are a modified body of the above and are capable of acting as a fibroblast growth factor. As the modified body of bFGF, those in which amino acid is added, substituted, or deleted in the amino acid sequence of bFGF which was obtained by the above-mentioned extraction or genetic engineering procedure, can be mentioned.

The bFGF which can be used in the present invention includes preferably, for example, those which were described in WO87/01728 and WO89/04832, and particularly those described in the former.

An amount of the cell growth factor in the vessel embolic material of the present invention may vary depending on an affected part, significance of diseases, conditions of a patient, and the like, and, for example, is 0.1 to 1,000 μg, preferably 2 to 500 μg, and more preferably 10 to 300 μg in the hydrogel administrated to the affected part.

The vessel embolic material of the present invention can change a discharge rate of the cell growth factor which is an effective ingredient depending on the property of the hydrogel used, in particular, properties of a material for preparing the hydrogel, a degree of crosslinking of the hydrogel material and a water content of the hydrogel. The discharge rate of the cell growth factor or a rate of decomposition or absorption of the hydrogel itself is an important factor of deciding the occlusion property of vessel lumen through the formation and neogenesis of an organism tissue by the growth of self cell. The present invention can successfully control these factors, namely decomposition of the hydrogel and sustained release of the cell growth factor, and can design the optimum embolic material for a site to be applied.

The treatment method of the present invention is carried out by introducing the above-mentioned vessel embolic material to the affected vessel site to which the embolic operation should be carried out, or around thereof, and the effect of the treatment of the present invention can be obtained thereby. The vessel embolic material can be introduced in an affected vessel part transdermally, or through a blood vessel using a catheter, or can be used by being placed in the affected blood vessel or at the peripheral thereof at operation. A form and amount used of the vessel embolic material can be appropriately selected by a size, form and the like of the site to be applied.

The vessel embolic material of the present invention can be used for the treatment of blood vessel disorder, specifically, treatments such as blood vessel deformities (for example, arteriovenous aneurysm, arteriovenous malformation, spinal arteriovenous malformation, meningeal arteriovenous fistula) such as brain, abdomen and the like, tumor, hemostasis and the like. In particular, it can be preferably used as an embolic material for treatment for aneurysm.

The vessel embolic material of the present invention may be used alone itself, or may be used in combination with a material or a method which is used in other embolic operation, for example, a coil made of platinum, or a stent.

EXAMPLES

The present invention is further illustrated below according to Examples, but the present invention is not limited by these.

(Preparation of Hydrogel)

A gelatin hydrogel containing bFGF was prepared according to the method described in WO94/27630. Specifically, 0.2 ml or 0.5 ml of a glutaraldehyde aqueous solution (10 W/V %) was each added to 20 ml of a gelatin aqueous solution (5 W/V %) having an isoelectric point of 4.9 which had been treated by an alkali, and the mixture was left to stand at room temperature over day and night to be cross-linked. Then, each product was immersed in 100 mM of a glycine aqueous solution at 37° C. for one hour. After completion of the reaction, each hydrogel was washed 3 times with distilled water at 37° C. for every one hour. According to the sequential operation, gelatin hydrogels having water content of 98% by weight and 95% by weight were obtained. In these hydrogels after drying, 50 mM of a phosphate buffer solution containing bFGF was added dropwise to be contained.

(Experiment)

A Japanese white rabbit (purchased from SHIMIZU LABORATORY SUPPLIES CO., LTD.) with a body weight of 3.0 kg was used for the experiment.

Under Nembutal narcosis, a right carotid artery and a right jugular vein were exposed. The jugular vein was bound, blood flow was stopped, and a vein piece with a length of 1 cm was cut. The blood flow of the carotid artery running in parallel was temporarily stopped by a clip, and an incision having a length of 5 cm was prepared at the wall of the blood vessel of the hemostasis part. One end of the vein piece, which was previously cut was stitched with the incision opening. After the gelatin hydrogels (water content: 98% and 95%) (3×3×3 mm) containing 100 μg of bFGF which was obtained above was wrapped with a gauze for operation, they were inserted into a blood vessel from an open end of the stitched vein piece. Then, the end of the open vein was anastomosed and closed. According to these serial operational manipulation, an experimental aneurysm with a diameter of 5 mm and a length of about 5 mm comprising a vein, which was protruded in a chimney shape at the side-wall of a carotid artery, was prepared.

According to the similar manner, an aneurysm being a control was prepared by inserting the gelatin hydrogel (water content: 98%) containing no bFGF.

(Result)

Figure 2:
FIG. 2 is a photograph showing the inner surface of a blood vessel of the experimental aneurysm treated with a gelatin hydrogel (water content: 98%) containing bFGF.
Figure 3:
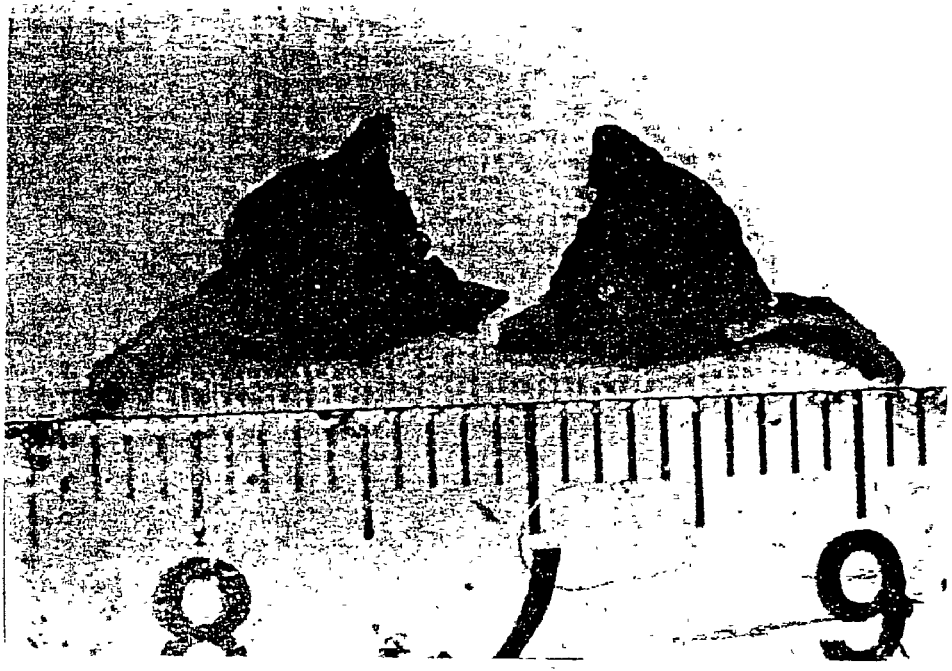
FIG. 3 is a photograph showing the inside of the experimental aneurysm treated with a gelatin hydrogel (water content: 95%) containing bFGF.
Figure 4:
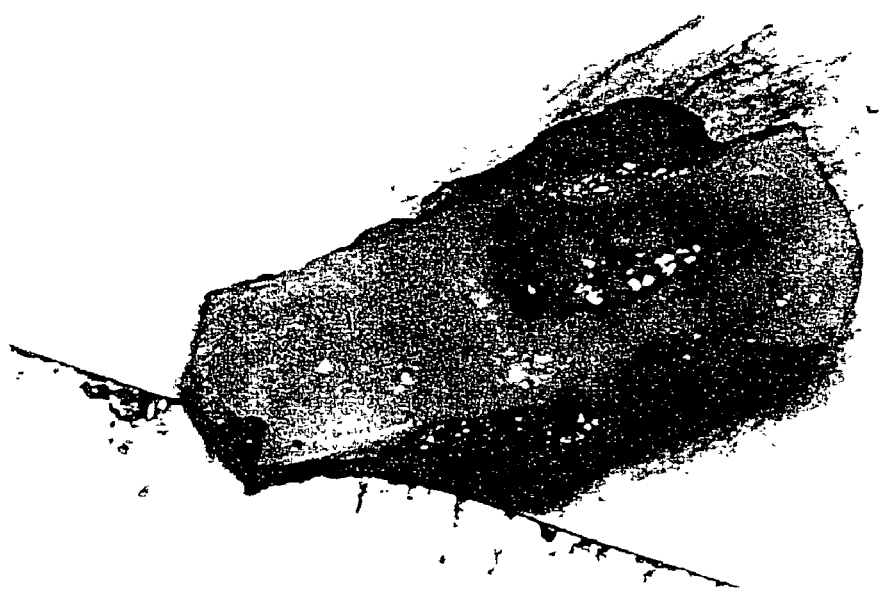
FIG. 4 is a photograph showing the inner surface of a blood vessel of the experimental aneurysm treated with a gelatin hydrogel (water content: 95%) containing bFGF.

The experimental aneurysm was taken out after 3 weeks from the administration and observed, and as a result, the inside of the aneurysm was filled with neogenesis tissue in case of the group treated with the gelatin hydrogels containing bFGF irrespective of the water content of the hydrogels. A panctum was not also observed at the portion to which the vein was anastomosed, and the tissue in the inner surface of the blood vessel had also similar appearance as that of the peripheral tissue. Incidentally, FIG. 1 is a photograph showing the inside of the experimental aneurysm treated with the gelatin hydrogel (water content: 98%) containing bFGF, FIG. 2 is a photograph showing the inner surface of the blood vessel of the experimental aneurysm treated with the gelatin hydrogel (water content: 98%) containing bFGF, and FIG. 3 is a photograph showing the inside of the experimental aneurysm treated with the gelatin hydrogel (water content: 95%) containing bFGF. Further, FIG. 4 is a photograph showing the inner surface of the blood vessel of the experimental aneurysm treated with the gelatin hydrogel (water content: 95%) containing bFGF.

Figure 5:
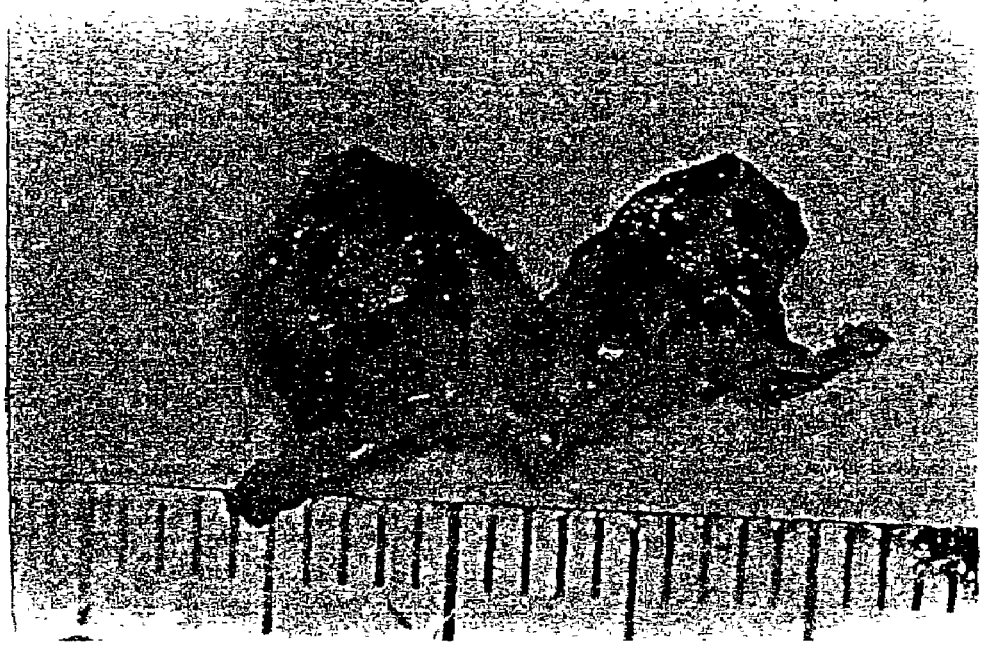
FIG. 5 is a photograph showing the inside of the experimental aneurysm treated with a gelatin hydrogel (water content: 98%) not containing bFGF (control).
Figure 6:
FIG. 6 is a photograph showing the inner surface of a blood vessel of the experimental aneurysm treated with a gelatin hydrogel (water content: 98%) not containing bFGF (control).

On the other hand, the inside of the experimental aneurysm remained a cavity in case of the group treated with the gelatin hydrogel containing no bFGF, and was not occluded. Incidentally, FIG. 5 is a photograph showing the inside of the experimental aneurysm treated with the gelatin hydrogel (water content: 98%) containing no bFGF (control), and FIG. 6 is a photograph showing the inner surface of blood vessel of the experimental aneurysm treated with the gelatin hydrogel (water content: 98%) containing no bFGF (control).

(Photograph of Tissue Fragment)

Figure 7:
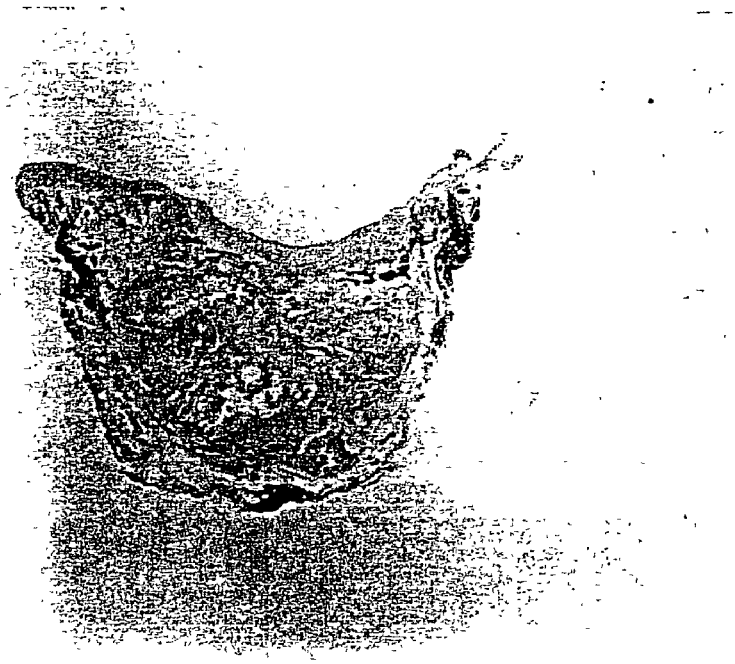
FIG. 7 is a photograph showing the tissue fragment of the experimental aneurysm treated with a gelatin hydrogel (water content: 98%) containing bFGF.
Figure 8:
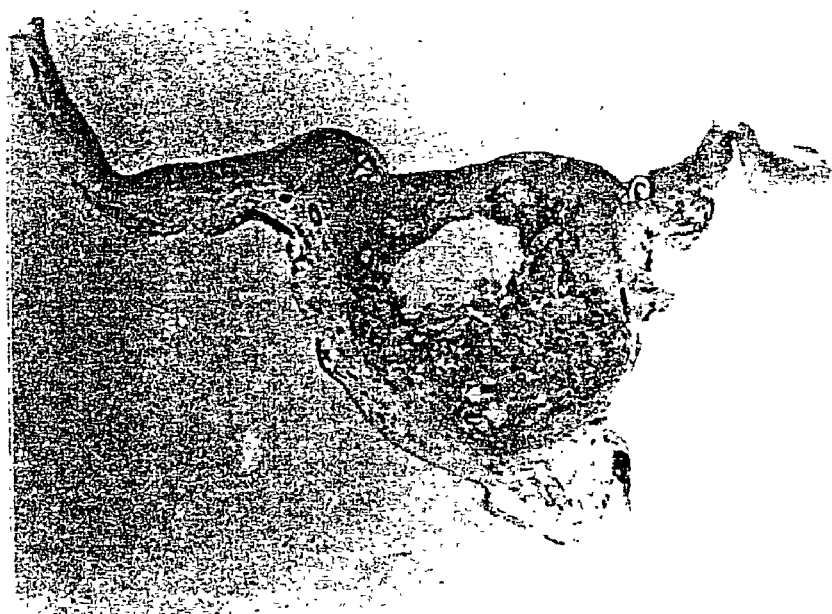
FIG. 8 is a photograph showing the tissue fragment of experimental aneurysm treated with a gelatin hydrogel (water content: 95%) containing bFGF.

The experimental aneurysms taken out were fixed with formalin, and fragments were prepared after wrapping them with paraffin. The photographs of the tissue fragments obtained by being stained with a hematoxylin-eocin staining method were shown in FIG. 7 and FIG. 8. Incidentally, FIG. 7 is a photograph showing the tissue fragment of the experimental aneurysm treated with the gelatin hydrogel (water content: 98%) containing bFGF, and FIG. 8 is a photograph showing the tissue fragment of the experimental aneurysm treated with the gelatin hydrogel (water content: 95%) containing bFGF.

In cases of the gelatin hydrogels having any water content which contain bFGF, the inside of the aneurysm was filled with neogenesis tissue, no dissection opening was observed at all at the anastomotic part of the artery and vein, and the reproduction of the same vascular endotheliocyte as the peripheral artery was admitted. The hollow portion in the drawing is a portion in which the hydrogel existed, and a hole is generated because the hydrogel was removed during preparation of the fragment. In case of a water content of 95%, it is also grasped that the hydrogel remains at this stage, and the excellent effect on vessel embolus can be observed.

(Area of Tissue)

Figure 9:
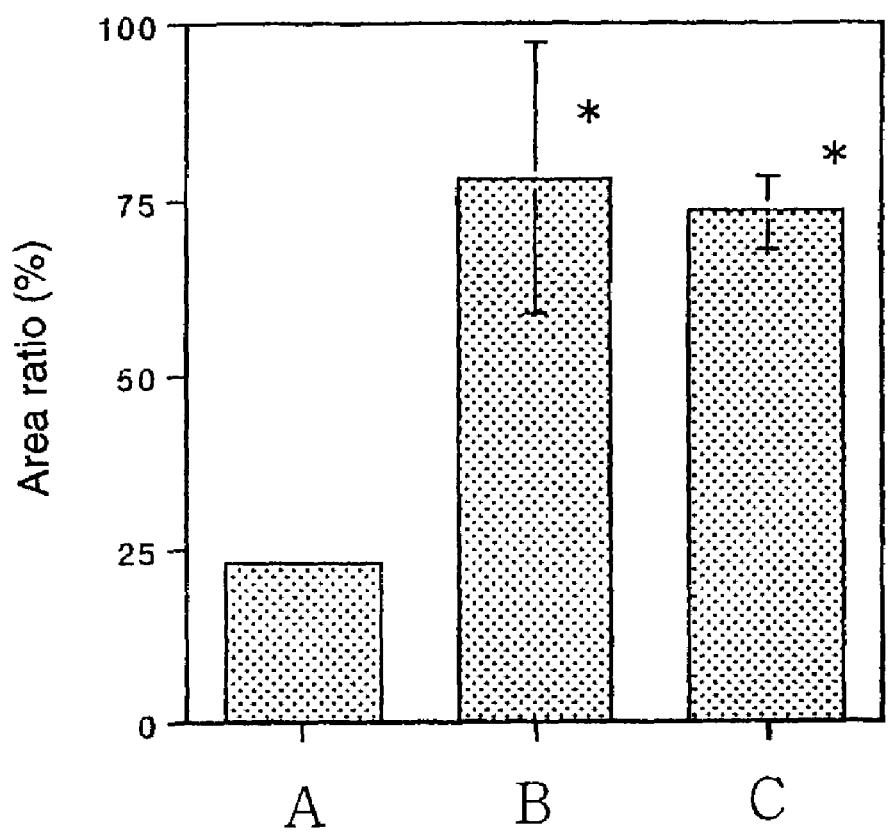
FIG. 9 is a graph showing the ratio of a tissue area, which was introduced by a gelatin hydrogel containing bFGF or a gelatin hydrogel not containing bFGF, to the total area of aneurysm.

A ratio of neogenesis tissue area, which was induced in the experimental aneurysm by a gelatin hydrogel containing bFGF to the total area of the experimental aneurysm was directly measured from the tissue fragment of the experimental aneurysm after 3 weeks of the treatment. The results of different three rabbits were shown in an average ±standard deviation. The results are shown in FIG. 9. Incidentally, in the drawings, A shows the hydrogel (water content: 98%) containing no bFGF, B shows the hydrogel (water content: 98%) containing bFGF, and C shows the hydrogel (water content: 95%) containing bFGF, respectively.

The group treated with the gelatin hydrogel containing bFGF showed the value of a significantly higher area ratio against the gelatin hydrogel containing no bFGF, irrespective of the water content of the hydrogel. (*: $p<0.05$)

INDUSTRIAL APPLICABILITY

Since the vessel embolic material of the present invention can gradually release the cell growth factor from the hydrogel which can be absorbed by a living body, it is excellent in adaptability to a living body and easily treated, can surely occlude the affected part, and has an effect that it can keep occlusion for a long time, and therefore, it is useful as a vessel embolic material for treating vessel disorders such as aneurysm, arteriovenous malformation and the like.

Further, the vessel embolic material of the present invention does not physically occlude the affected part of a blood vessel by an artificial article or thrombus in like manner as a conventional embolic material or an embolic method, aggressively forms self organism tissue in vessel lumen, and enables the sure occlusion thereby.

Further, according to the treatment of vessel disorders of the present invention, it excellent in adaptability to a living body and easily treated, can surely occlude the affected part, and has an effect that it can keep occlusion for a long time, therefore can effectively treat the vessel disorders such as aneurysm, arteriovenous malformation and the like.

The invention claimed is:

1. A method of treating an aneurysm comprising applying a cross-linked gelatin hydrogel containing bFGF to an affected blood vessel site wherein the aneurysm is located and wherein the cross-linked gelating hydrogel containing bFGF gradually releases bFGF resulting in occlusion of the lumen of the affected blood vessel site thereby treating the aneurysm and further wherein the aneurysm is an aneurysm in a form of a protrusion or a knob of size 1-20 mm.

2. The method of treating an aneurysm according to claim 1, wherein the cross-linked gelatin hydrogel is an alkali treated gelatin having an isoelectric point of 4.9 or an acid treated gelatin having an isoelectric point of 9.0.

3. The method of treating an aneurysm according to claim 1, wherein the cross-linked gelatin hydrogel is a material in which gelatin is cross-linked by glutaraldehyde or 1-ethyl-3-(3-dimethylaminopropyl) carbodiimide hydrochloride.

4. The method of treating an aneurysm according to claim 1, wherein the cross-linked gelatin hydrogel is a material in which gelatin is cross-linked by a heat-treatment or irradiation of UV-rays.

5. The method of treating an aneurysm according to claim 1, wherein the hydrogel has a shape of rectangular, cylindrical, sheet, disc, sphere, or granular.

6. The method of treating an aneurysm according to claim 1, wherein a water content of the hydrogel is about 50 to 99 w/w %.

7. The method of treating an aneurysm according to claim 1, wherein the bFGF is contained in an amount of 0.1 to 1,000 μg in the hydrogel to be administered to the affected blood vessel or around the affected blood vessel site.

* * * * *